(12) United States Patent
Perdrieux et al.

(10) Patent No.: US 8,350,101 B2
(45) Date of Patent: Jan. 8, 2013

(54) METHOD FOR PREPARING VINYLIDENE FLUORIDE

(75) Inventors: Sylvain Perdrieux, Charly (FR); Serge Hub, Villeurbanne (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 13/123,353

(22) PCT Filed: Aug. 20, 2009

(86) PCT No.: PCT/FR2009/051611
§ 371 (c)(1),
(2), (4) Date: Jun. 23, 2011

(87) PCT Pub. No.: WO2010/043792
PCT Pub. Date: Apr. 22, 2010

(65) Prior Publication Data
US 2012/0130136 A1   May 24, 2012

(30) Foreign Application Priority Data
Oct. 13, 2008  (FR) ..................................... 08 56898

(51) Int. Cl.
*C07C 17/25*  (2006.01)

(52) U.S. Cl. .......................... 570/155; 570/136; 570/153
(58) Field of Classification Search ........................ None
See application file for complete search history.

(56) References Cited

U.S. PATENT DOCUMENTS

| 2,628,989 | A | * | 2/1953 | Miller ........................... 570/156 |
| 2,774,798 | A |   | 12/1956 | Davis et al. |
| 2,774,799 | A |   | 12/1956 | Mantell et al |
| 3,183,277 | A |   | 5/1965 | Scherer et al |
| 4,053,529 | A | * | 10/1977 | Martens ......................... 570/155 |
| 5,068,473 | A |   | 11/1991 | Kellner et al. |
| 5,146,018 | A |   | 9/1992 | Kellner et al. |
| 5,315,045 | A | * | 5/1994 | Berthe et al. .................. 570/153 |

FOREIGN PATENT DOCUMENTS
GB    2165241    4/1986

* cited by examiner

*Primary Examiner* — Sudhakar Katakam
(74) *Attorney, Agent, or Firm* — Thomas F. Roland

(57) ABSTRACT

The present invention relates to the method for obtaining vinylidene fluoride and the subject matter thereof is more particularly the production of vinylidene fluoride by pyrolysis of 1,2-dichloro-2,2-difluoroethane in the presence of hydrogen at a temperature of greater than or equal to 400° C.

8 Claims, No Drawings

METHOD FOR PREPARING VINYLIDENE FLUORIDE

The present invention relates to the field of unsaturated fluorohydrocarbons, and the subject thereof is more particularly the synthesis of vinylidene fluoride ($VF_2$) from 1,2-dichloro-2,2-difluoroethane (F132b).

Fluoroolefins, such as $VF_2$, are known and are used as monomers or comonomers for the production of fluorocarbon-based polymers having notable characteristics, in particular excellent chemical resistance and good thermal resistance.

$VF_2$ can be produced by dehydrohalogenation, either of 1,1,1-chlorodifluoroethane (F142b) by a loss of HCl, or of 1,1,1-trifluoroethane (F143a) by a loss of HF, The processes implemented have the drawback of using, as reactants, entities resulting from the total or partial hydrofluorination of 1,1,1-trichloroethane, to which there is limited access.

Finally, $VF_2$ can be obtained from 1-chloro-2,2-difluoroethane (F142) originating from the partial hydrofluorination of 1,1,2-trichloroethane, which is more readily available. Thus, document U.S. Pat. No. 2,774,799 describes a process for obtaining vinylidene fluoride by heating difluorochloroethane at a temperature of between 500 and 730° C. and with a contact time of between 1 and 60 seconds in the presence of copper metal and of alloys thereof.

$VF_2$ can also be produced by catalytic dehydrohalogenation of 1,2-dichloro-2,2-difluoroethane (F132b) in the presence of hydrogen via the loss of two molecules of HCl. Example 4 of document EP485246 describes the use of a mixed catalyst of palladium and copper deposited on carbon. It is also possible to use alkali metal amalgams, as mentioned in the patent GB2165241, but the process then generates salt that needs to be processed, eliminated or recovered.

The catalytic processes have many drawbacks, such as the preparation of the catalyst, the activation and the initiation of a new catalyst, the deactivation of the catalyst, the risk of blocking of the reactor loaded with catalyst owing to the formation of polymeric by-products, and the elimination of the spent catalysts. The present invention provides a process for obtaining vinylidene fluoride in the absence of catalyst. More particularly, the process according to the present invention comprises the pyrolysis of 1,2-dichloro-2,2-difluoroethane in the presence of hydrogen at a temperature of greater than or equal to 400° C., so as to give vinylidene fluoride. Preferably, the temperature is between 400 and 1000° C., advantageously between 450 and 750° C., and more particularly at a temperature of between 500 and 600° C.

The term "pyrolysis" is intended to mean a chemical conversion under the effect of temperature in the absence of catalyst.

Pyrolysis reactors generally comprise three zones: (a) the preheating zone in which the reactants are brought into contact at a temperature close to that of the reaction, (b) the reaction zone in which the reactants are at the reaction temperature and are at least partially converted to products and by-products and (c) a quenching zone in which the stream resulting from the reaction zone is cooled so as to stop the pyrolysis reaction. On the laboratory scale, the reactors can comprise only the reaction zone; the preheating and quenching zones can be ignored.

According to the present invention, the reaction for pyrolysis of 1,2-dichloro-2,2-difluoroethane in the presence of hydrogen is carried out in the absence of catalyst in an essentially empty reactor. The term "absence of catalyst" is intended to mean the fact that there has been no addition of material or processing in the reactor in order to increase the reaction rate by reducing the activation energy of the process.

More particularly, the term "absence of catalyst" is intended to mean absence of conventional catalyst having a specific surface area and which is in the form of particles or of extrudates, and which is optionally supported so as to facilitate the dehydrochlorination reaction.

The essentially empty reactors which are suitable are quartz, ceramic (SiC) or metallic reactors. In this case, the material constituting the reactor can be chosen from metals such as nickel, iron, titanium, chromium, molybdenum, cobalt or gold, or alloys thereof. The metal, chosen more particularly to limit corrosion or catalytic phenomena, may be bulk metal or metal plated onto another metal.

The essentially empty reactors that can be used in the present invention may comprise baffles or packings that are inert, such as Raschig rings, to facilitate mixing of gases.

The hydrogen/F132b molar ratio can be between 0.2 and 20, preferably between 0.5 and 10, and advantageously between 1 and 6.

In addition to the reactants, the reaction can be carried out in the presence of an inert gas such as nitrogen, helium and argon.

The contact time, defined as being the ratio between the volume of the empty reactor and the volume flow rate of the gas stream under the normal temperature and pressure conditions, can be between 0.1 and 500 seconds, and preferably between 0.5 and 100 seconds, and advantageously between 1 and 50 seconds.

Industrially, it is preferable to work at atmospheric pressure, but working at a pressure below or above atmospheric pressure would not depart from the context of the present invention provided that the reaction system remains in the gaseous state.

The following examples illustrate the invention without limiting it.

EXAMPLE 1

A mixture of hydrogen and F132b is fed into an electrically heated stainless steel tubular reactor 45 cm long and with an internal diameter of 10 mm, under the following conditions:

| | |
|---|---|
| Pressure: | atmospheric |
| Temperature: | 550° C. |
| Flow rate of F132b: | 0.047 mol/h |
| Flow rate of hydrogen: | 0.094 mol/h |
| $H_2$/F132b ratio: | 2 molar |
| Residence time: | 13.4 s |

The analysis is carried out by gas chromatography (GC) on the gases derived from the reactor. The identification of the product was confirmed by mass spectrometry.

The major product of the reaction is $VF_2$. The F132b conversion rate is 84% and the selectivity with respect to $VF_2$ is 86%.

The conversion rate is the percentage of the starting product having reacted (number of moles of the starting product having reacted/number of moles of the starting product introduced).

The selectivity with respect to desired product is the ratio of the number of moles of desired product/number of moles of starting product having reacted.

EXAMPLE 2

The process is carried out as in example 1, except that the flow rate of F132b is 0.094 mol/h and the flow rate of hydrogen is 0.375 mol/h and the hydrogen/F132b molar ratio is 4.

The contact time is 4 sec.

The F132b conversion rate is 73% and the selectivity with respect to $VF_2$ is 87%.

EXAMPLE 3

The process is carried out as in example 2, except that the temperature is 600° C.

The F132b conversion rate is 97% and the selectivity with respect to $VF_2$ is 82%.

The invention claimed is:

1. A process for obtaining vinylidene fluoride, consisting of the pyrolysis of 1,2-dichloro-2,2-difluoroethane in the presence of hydrogen in the absence of a catalyst at a temperature of greater than or equal to 400° C.

2. The process as claimed in claim 1, wherein the temperature is between 400 and 1000° C.

3. The process as claimed in claim 1 wherein the temperature is between 450 and 750° C.

4. The process as claimed in claim 1, wherein the temperature is between 500 and 600° C.

5. The process as claimed in claim 1, wherein the hydrogen/1,2-dichloro-2,2-difluoroethane molar ratio is between 0.2 and 20.

6. The process as claimed in claim 1, wherein the hydrogen/1,2-dichloro-2,2-difluoroethane molar ratio is between 0.5 and 10.

7. The process as claimed in claim 1, wherein the hydrogen/1,2-dichloro-2,2-difluoroethane molar ratio is between 1 and 6.

8. The process as claimed in claim 1, wherein pyrolysis is carried out in the presence of an inert gas.

* * * * *